(12) United States Patent
Gupta et al.

(10) Patent No.: US 7,371,903 B2
(45) Date of Patent: May 13, 2008

(54) 2-BUTANOL PRODUCTION METHOD

(75) Inventors: Antje Gupta, Wiesbaden (DE); Anke Tschentscher, Etville am Rhein (DE); Maria Bobkova, Idstein (DE)

(73) Assignee: IEP GmbH, Wiesbaden (DE)

( * ) Notice: Subject to any disclaimer, the term of this patent is extended or adjusted under 35 U.S.C. 154(b) by 0 days.

(21) Appl. No.: 11/568,905

(22) PCT Filed: Apr. 29, 2005

(86) PCT No.: PCT/IB2005/001556

§ 371 (c)(1),
(2), (4) Date: Jul. 20, 2007

(87) PCT Pub. No.: WO2005/108593

PCT Pub. Date: Nov. 17, 2005

(65) Prior Publication Data

US 2007/0265477 A1 Nov. 15, 2007

(30) Foreign Application Priority Data

May 10, 2004 (AT) ............................... A 800/2004

(51) Int. Cl.
*C07C 29/143* (2006.01)
(52) U.S. Cl. ..................................... 568/880; 568/913

(58) Field of Classification Search .................... None
See application file for complete search history.

(56) References Cited

U.S. PATENT DOCUMENTS

| 5,342,767 | A | | 8/1994 | Wong et al. | |
| 5,523,223 | A | * | 6/1996 | Kula et al. | .................. 435/189 |

FOREIGN PATENT DOCUMENTS

| EP | 1 323 827 A | 7/2003 |
| WO | 9318138 | 9/1993 |
| WO | 2004111083 | 12/2004 |
| WO | 2005049816 | 6/2005 |

* cited by examiner

*Primary Examiner*—Sikarl A. Witherspoon
(74) *Attorney, Agent, or Firm*—Workman Nydegger

(57) ABSTRACT

The invention relates to a process for the preparation of 2-butanol by enzymatic-catalyzed reduction of 2-butanone with a carbonyl reductase and a coenzyme and is characterized in that an aqueous phase, which contains the carbonyl reductase and the coenzyme, is contacted with an alcoholic phase, which is not miscible with the aqueous phase and contains 2-butanone, in order to reduce the 2-butanone, with the proviso that the alcohol present in the alcoholic phase is a secondary alcohol capable of regenerating the coenzyme and exhibiting a boiling point which lies above that of water, whereupon the 2-butanol formed is separated.

19 Claims, No Drawings

2-BUTANOL PRODUCTION METHOD

This application is the national stage of PCT/IB05/01556, filed Apr. 29, 2005, and published as WO 2005/108593 on Nov. 17. 2005.

The invention relates to a process for the preparation of 2-butanol and in particular R-2-butanol and S-2-butanol by enzymatic-catalyzed reduction of 2-butanone with a carbonyl reductase and a coenzyme.

2-Butanol and in particular the chiral compounds R-2-butanol and S-2-butanol are desirable intermediates sought after in the production of pharmaceutically active substances.

The preparation of enantiomerically pure 2-butanol, i.e. R-2-butanol and S-2-butanol, is complex since, to date, a direct chemical, catalytic asymmetric reduction of 2-butanone to R— or S-2-butanol, respectively, has not been possible. Processes for a direct enzymatic reduction have so far not been described, either. Enantiomerically pure R-2-butanol and S-2-butanol can be produced on a commercial scale only by indirect means via racemate resolution.

Carbonyl reductases (further names: alcohol dehydrogenases, oxidoreductases) are known as catalysts for the reduction of carbonyl compounds and for the oxidation of secondary alcohols, respectively. Those enzymes require a coenzyme, for instance, NAD(P)H. The reduction of ketones with the carbonyl reductase obtained from Lactobacillus kefir and with the coenzyme NADPH is known, for example, from U.S. Pat. No. 5,342,767.

The purification and characterization of an alcohol dehydrogenase from *Moraxella* sp. is known from Eur. J. Biochem. 254, 356-362 (1998).

The reduction of 2-butanone to 2-butanol by means of carbonyl reductase in an aqueous medium is difficult, since the reprocessing of the reaction mixture is not easy and 2-butanol is readily soluble in water. In addition, extraction and distillation processes for the separation of 2-butanol and water prove to be technically complex.

A further problem associated with the enzymatic reduction of 2-butanone to 2-butanol by means of carbonyl reductase consists in the regeneration of the cofactor NADH or NADPH, respectively. The method of regenerating the NAD(P)H with 2-propanol, which is often used at present, likewise is problematic here, since the latter renders even more difficult the isolation of the product R— or S-2-butanol, respectively, and, moreover, cannot be separated completely from the R— or S-2-butanol, respectively, without extreme effort.

An additional problem associated with the enzymatic reduction of 2-butanone in an aqueous medium, along with a coenzyme regeneration of the NAD(P)H with 2-propanol, consists in the inactivation of most enzymes at a 2-propanol and 2-butanol content of more than 20%. That means that the final concentration of the 2-butanone to be used has to lie far below 10% (w/v) when starting out from an excess of 2-propanol to be used. These low substrate or product concentrations which are feasible in turn hamper the isolation of the R— or S-2-butanol, respectively, from the reaction mixture.

The process according to the invention for the preparation of 2-butanol by enzymatic-catalyzed reduction of 2-butanone with a carbonyl reductase and a coenzyme has the object of solving the above-mentioned problems and is characterized in that (a) an aqueous phase, which contains the carbonyl reductase and the coenzyme, is contacted with an alcoholic phase, which is not miscible with the aqueous phase and contains 2-butanone, in order to reduce the 2-butanone, with the proviso that the alcohol present in the alcoholic phase is a secondary alcohol capable of regenerating the coenzyme and exhibiting a boiling point which lies above that of water, whereupon (b) the 2-butanol formed is separated.

In the process according to the invention, the reaction of 2-butanone to 2-butanol by means of carbonyl reductase is thus carried out in a two-phase system consisting of an aqueous phase in which the enzyme and the coenzyme are dissolved and an organic phase formed from the secondary alcohol and 2-butanone.

Coenzyme regeneration is conducted with a secondary alcohol which is not miscible with water and, at the same time, exhibits a boiling point which, as much as possible, is clearly higher than that of water. Thereby, 2-pentanol, 2-hexanol, 2-heptanol, 2-octanol and 4-methyl-2-pentanol have proven to be advantageous, amongst which 2-heptanol and 2-octanol are preferred.

NADH and NADPH are particularly suitable as coenzymes. In addition, the secondary alcohol not miscible with water leads to a stabilization of the carbonyl reductase in the process according to the invention.

The advantage of using a secondary alcohol not miscible with water for the coenzyme regeneration also consists in that said alcohol may be used in a higher excess with respect to the substrate 2-butanone to be reduced. It thus becomes feasible to achieve a higher turnover along with higher concentrations of 2-butanone in the feedstock. Therefore, the secondary alcohol of the alcoholic phase and the 2-butanone are preferably used at a molar ratio ranging from 1:2 to 1:10 (2-butanone:secondary alcohol), with a molar ratio ranging from 1:2.5 to 1:5 being particularly preferred.

A further embodiment of the process according to the invention consists in that the 2-butanone is used in an amount of at least 5% by volume, preferably ranging from 10-25% by volume, based on the total reaction mixture.

The carbonyl reductase will preferably be used in an amount of at least 2,000 units, preferably, however, of at least 10,000 units, of carbonyl reductase per kg of 2-butanone, with the upper limit suitably amounting to 250,000 units of carbonyl reductase per kg of 2-butanone. Thereby, the enzyme unit 1 U corresponds to the enzyme amount which is required for converting 1 μmol of 2-butanone per minute (min).

Especially that derived from *Candida parapsilosis* has proven to be a valuable carbonyl reductase or alcohol dehydrogenase, respectively. Preferably, a carbonyl reductase is used which permits the preparation of substantially enantiomerically pure S-2-butanol or R-2-butanol. In doing so, it has been found that the carbonyl reductase from *Candida parapsilosis* is capable of reducing 2-butanone stereoselectively to S-2-butanol, whereby, depending on the chosen process conditions, an enantiomeric purity above 98% of the desired enantiomer is achievable.

The 2-butanol formed in the process according to the invention is in the phase of the secondary alcohol and may be decanted from the aqueous phase together with said alcohol. Subsequently, the 2-butanol can be obtained in an simple manner via distillation.

In the process according to the invention, the corresponding enantiomerically pure S-alcohol could also be used for the coenzyme regeneration.

The amount of the aqueous and organic phases with respect to the total volume of the reaction mixture is open to variations, wherein the amount of the aqueous phase can be reduced down to 3% by volume, resulting in that more than 90% of the employed 2-butanone or of the R— or S-2- butanol, respectively, are located in the phase formed by the alcohol not miscible with water.

A further advantage of the process according to the invention consists in the comparatively simple reprocessing and isolation of the R— or S-2-butanol, respectively, in highly purified form. The isolation of the product R— or S-2-butanol, respectively, is performed by separating the organic phase and by distilling the 2-butanone/2-butanol from the high-boiling secondary alcohol not miscible with water.

Subsequently, the chiral product R— or S-2-butanol, respectively, can be recovered from the 2-butanol/2-butanone mixture via distillation in a chemical purity >99% and an enantiomeric purity >98%.

In the process according to the invention, the concentration to be used for the substrate 2-butanone preferably lies above 5% by volume, particularly preferably ranging from 10% by volume to 25% by volume.

The concentration of the coenzyme NAD(P)H, based on the aqueous phase, is from 0.01 to 10 mM, in particular from 0.1 to 1 mM.

Preferably, a buffer, for example a potassium phosphate, tris/HCl or triethanolamine buffer having a pH value of 5 to 10, preferably a pH value of 6 to 9, is added to the aqueous phase used in the process.

In the process according to the invention, the carbonyl reductase can either be purified completely or partially or can be used in the form of cell lysates or in the form of whole cells. Thereby, the cells being used can be provided in the native or in the permeabilized state.

The temperature is from, e.g., about 10° C. to 60° C., preferably from 25° C. to 35° C.

The process according to the invention can be carried out, for example, in a closed reaction vessel made of glass or metal. For that purpose, the components are transferred individually into the reaction vessel and are stirred under an atmosphere of, e.g., nitrogen or air. The reaction time amounts to 1 to 48 hours, in particular to 2 to 24 hours. Instead of the carbonyl reductase from Candida parapsilosis, other carbonyl reductases might be used as well which are capable of reducing 2-butanone enantioselectively to S-2-butanol or R-2-butanol.

By way of the following examples, the invention will be described in greater detail.

EXAMPLE 1

In this example, the production of S-2-butanol from 2-butanone and the dependence of the yield of S-2-butanol depending on the employed ratio of 2-butanone/secondary alcohol (2-heptanol) is shown. As the carbonyl reductase, that from *Candida parapsilosis* was used. Coenzyme regeneration was conducted with 2-heptanol. In the following Table 1, the conversion data for three feedstocks exhibiting different 2-butanone/2-heptanol ratios are shown.

TABLE 1

|  | Feedstock 1 | Feedstock 2 | Feedstock 3 |
| --- | --- | --- | --- |
| Composition |  |  |  |
| Buffer (100 mM TEA pH = 7.0) | 1 ml | 1 ml | 1 ml |
| 2-Butanone | 2.5 ml (0.027 mol) | 2.5 ml (0.027 mol) | 2.5 ml (0.027 mol) |
| NAD | 0.5 mg | 0.5 mg | 0.5 mg |
| 2-Heptanol | 10 ml (0.068 mol) | 15 ml (0.103 mol) | 20 ml (137 mol) |
| ADH from *Candida parapsilosis* | 60 units | 60 units | 60 units |
| Parameters |  |  |  |
| Volume | 13.5 ml | 18.5 ml | 23.5 ml |
| Molar ratio 2-butanone/2-heptanol | 1:2.5 | 1:3.8 | 1:5 |
| Concentration 2-butanone in % (v/v) | 18.5% | 13.5% | 10.6% |
| Yield (% S-butanol) | 43% | 61% | 70% |
| Enantiomeric purity S-butanol | 99% S | 99% S | 99% S |

The conversion was performed by first placing the buffer in the reaction vessel in which then the NAD and the enzyme were dissolved. Subsequently, the 2-heptanol and the 2-butanone were placed in the reaction vessel.

The reaction mixture was then incubated at 30° C. while being mixed thoroughly. The reaction was terminated once no further conversion of 2-butanone was observed and thus the reaction equilibrium had been achieved.

In Table 1, it can be seen that the yield of S-2-butanol increases substantially with an increasing concentration of 2-heptanol.

EXAMPLE 2

In this example, it is shown by way of three feedstocks that the aqueous phase can be reduced without substantially changing the yield.

TABLE 2

|  | Feedstock 4 | Feedstock 5 | Feedstock 6 |
| --- | --- | --- | --- |
| Composition |  |  |  |
| Buffer (100 mM TEA pH = 7.0) | 2.5 ml | 5 ml | 10 ml |
| 2-butanone | 5 ml (0.054 mol) | 5 ml (0.054 mol) | 5 ml (0.054 mol) |
| NAD | 1 mg | 1 mg | 1 mg |
| 2-heptanol | 30 ml (0.206 mol) | 30 ml (0.206 mol) | 30 ml (0.206 mol) |
| ADH from *Candida parapsilosis* | 500 units | 500 units | 500 units |
| Parameters |  |  |  |
| Volume | 37.5 ml | 40 ml | 45 ml |
| Molar ratio 2-butanone/2-heptanol | 1:3.8 | 1:3.8 | 1:3.8 |
| Conc. 2-butanone in % (v/v) | 13.3% | 12.5% | 11% |
| Yield (% S-butanol) | 55% | 58% | 56% |
| Enantiomeric purity S-butanol | 98% S | 98% S | 98% S |

EXAMPLE 3

In this example, it is shown that the regeneration of the coenzyme can be carried out with different secondary alcohols. The results of three feedstocks are indicated in the following Table 3.

TABLE 3

|  | Feedstock 7 | Feedstock 8 | Feedstock 9 |
|---|---|---|---|
| Composition |  |  |  |
| Buffer (100 mM TEA pH = 7.0) | 20 ml | 20 ml | 6 ml |
| 2-Butanone | 5 ml (0.054 mol) | 5 ml (0.054 mol) | 1 ml (0.0108 mol) |
| NAD | 0.5 mg | 0.5 mg | 1 mg |
| Secondary alcohol | 30 ml 4-methyl-2-pentanol (0.23 mol) | 30 ml 2-hexanol (0.23 mol) | 4 ml 2-pentanol (0.036 mol) |
| ADH from *Candida parapsilosis* | 500 units | 500 units | 100 units |
| Parameters |  |  |  |
| Volume | 55 ml | 55 ml | 11 ml |
| Molar ratio 2-butanone/2-heptanol | 1:4.3 | 1:4.3 | 1:3.3 |
| Conc. 2-butanone in % (v/v) | 9% | 9% | 9% |
| Yield (% S-butanol) | 78% | 70% | 68% |
| Enantiomeric purity S-butanol | 96% S | 98% S | 98% S |

EXAMPLE 4

In this example, the preparative production of S-2-butanol on a technical scale is shown.

For the preparative production of S-2-butanol, 4.96 l of a buffer (TEA 100 mM, pH=7.0) were placed in a stirred reactor adjusted to a temperature of 30° C. Subsequently, 4.96 g of NAD were dissolved in the buffer and 300,000 units of carbonyl reductase from *Candida parapsilosis* were added to the buffer. The reaction mixture was covered with a layer of 76.11 l ( 60.9 kg) of 2-heptanol and thereupon the substrate 2-butanone, 12.5 l (10 kg), was added.

Subsequently, the stirring was switched on and the reaction mixture was incubated for 12 h while being mixed thoroughly. After 12 h, the 2-butanone was converted to S-2-butanol by 68%, involving an enantiomeric purity of 98.4%.

Upon completion of the reaction, the heptanol phase containing 2-butanone/S-2-butanol was separated and dried. The 2-butanone/S-2-butanol mixture was first obtained from the heptanol phase (boiling point approx. 158-161° C.) via distillation prior to the separation of 2-butanone (boiling point 80° C.) and S-2-butanol (boiling point=97-100° C.) in a second distillation.

In this manner, S-2-butanol could be obtained in a chemical purity >99%.

What is claimed is:

1. A process for the preparation of 2-butanol by enzymatic-catalyzed reduction of 2-butanone with a carbonyl reductase and a coenzyme, the process comprising:
   (a) an aqueous phase, which contains the carbonyl reductase and the coenzyme, is contacted with an alcoholic phase, which is not miscible with the aqueous phase and contains 2-butanone, in order to reduce the 2-butanone, with the proviso that the alcohol present in the alcoholic phase is a secondary alcohol capable of regenerating the coenzyme and exhibiting a boiling point which lies above that of water, whereupon
   (b) the 2-butanol formed is separated.

2. The process according to claim 1, wherein the alcohol of the alcoholic phase is selected from a group consisting of 2-pentanol, 2-hexanol, 2-heptanol, 2-octanol, and 4-methyl-2-pentanol.

3. The process according to claim 2, wherein the secondary alcohol of the alcoholic phase and the 2-butanone are used at a molar ratio ranging from about 1:2 to about 1:10 (2-butanone:secondary alcohol).

4. The process according to claim 3, wherein the molar ratio ranges from about 1:2.5 to about 1:5.

5. The process according to claim 2, wherein the alcohol of the alcoholic phase is 2-heptanol.

6. The process according to claim 5, wherein the secondary alcohol of the alcoholic phase and the 2-butanone are used at a molar ratio ranging from about 1:2 to about 1:10 (2-butanone:secondary alcohol).

7. The process according to claim 6, wherein the molar ratio ranges from about 1:2.5 to about 1:5.

8. The process according to claim 2, wherein the alcohol of the alcoholic phase is 2-octanol.

9. The process according to claim 8, wherein the secondary alcohol of the alcoholic phase and the 2-butanone are used at a molar ratio ranging from about 1:2 to about 1:10 (2-butanone:secondary alcohol).

10. The process according to claim 9, wherein the molar ratio ranges from about 1:2.5 to about 1:5.

11. The process according to claim 1, wherein the secondary alcohol of the alcoholic phase and the 2-butanone are used at a molar ratio ranging from about 1:2 to about 1:10 (2-butanone:secondary alcohol).

12. The process according to claim 11, wherein the molar ratio ranges from about 1:2.5 to about 1:5.

13. The process according to claim 1, wherein the 2-butanone is used in an amount of at least 5% by volume, preferably ranging from about 10-25% by volume, based on the total reaction mixture.

14. The process according to claim 1, wherein at least 2,000 units of carbonyl reductase per kg of 2-butanone are used.

15. The process according to claim 14, wherein at least 10,000 units of carbonyl reductase per kg of 2-butanone are used.

16. The process according to claim 1, wherein a carbonyl reductase obtainable from *Candida parapsilosis* is used.

17. The process according to claim 1, wherein the 2-butanol formed is separated by distillation.

18. The process according to claim 1, wherein a carbonyl reductase is used which permits the preparation of substantially enantiomerically pure S-2-butanol.

19. The process according to claim 1, wherein a carbonyl reductase is used which permits the preparation of substantially enantiomerically pure R-2-butanol.

* * * * *